(12) United States Patent
Shimada et al.

(10) Patent No.: US 8,033,986 B2
(45) Date of Patent: Oct. 11, 2011

(54) ENDOSCOPE CONTROL DEVICE

(75) Inventors: Atsushi Shimada, Hachioji (JP);
Yusuke Yabe, Hachioji (JP); Susumu Hashimoto, Hachioji (JP); Tomoya Takahashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1298 days.

(21) Appl. No.: 11/642,235

(22) Filed: Dec. 20, 2006

(65) Prior Publication Data

US 2007/0149847 A1 Jun. 28, 2007

(30) Foreign Application Priority Data

Dec. 28, 2005 (JP) .................................. 2005-379801

(51) Int. Cl.
*A61B 1/00* (2006.01)
*A61B 1/04* (2006.01)
*A61B 1/06* (2006.01)
(52) U.S. Cl. .................... 600/103; 600/118; 600/178
(58) Field of Classification Search .................. 348/68; 600/178–181
See application file for complete search history.

(56) References Cited

U.S. PATENT DOCUMENTS

| 4,611,271 A | 9/1986 | Hattori et al. |
| 5,181,011 A | 1/1993 | Okano |
| 5,894,322 A * | 4/1999 | Hamano et al. ................. 348/68 |
| 6,511,422 B1 * | 1/2003 | Chatenever .................... 600/180 |
| 2009/0187077 A1 * | 7/2009 | Hosoda et al. ................. 600/178 |

FOREIGN PATENT DOCUMENTS

| JP | 59-214953 | 12/1984 |
| JP | 61-248141 | 11/1986 |
| JP | 63-26899 | 2/1988 |
| JP | 64-076829 | 3/1989 |
| JP | 4-40014 | 7/1992 |
| JP | 7-289712 | 11/1995 |
| JP | 2000-369 | 1/2000 |
| JP | 2000-151388 | 5/2000 |
| JP | 2003-044303 | 2/2003 |
| JP | 2003-248595 | 9/2003 |
| JP | 2004-56716 | 2/2004 |
| JP | 2004-64585 | 2/2004 |
| JP | 2004-274727 | 9/2004 |

OTHER PUBLICATIONS

Extended European Search Report dated Mar. 11, 2011.

* cited by examiner

*Primary Examiner* — Philip Smith
(74) *Attorney, Agent, or Firm* — Scully, Scott, Murphy & Presser, P.C.

(57) ABSTRACT

An endoscope control device includes: a safety maintaining circuit for maintaining safety in terms of function or use-purpose of the endoscope control device; a control section for controlling operation of the endoscope control device; and an activation section for activating the control section, wherein the safety maintaining circuit is formed in the same device as at least one of the control section and the activation section.

6 Claims, 5 Drawing Sheets

US 8,033,986 B2

ENDOSCOPE CONTROL DEVICE

CROSS REFERENCE TO RELATED APPLICATION

This application claims the benefit of Japanese Application No. 2005-379801 filed on Dec. 28, 2005, the contents of which are incorporated by this reference.

BACKGROUND OF THE INVENTION

1. Field of the Invention

The present invention relates to an endoscope control device, and in particular, to an endoscope control device having a safety maintaining circuit.

2. Description of the Related Art

Conventionally, endoscopes have been widely used in the medical and industrial fields.

An insertion portion of an endoscope in an endoscope device is inserted into a body cavity, a thin vessel, and the like. The insertion portion is provided with a bending section which is bendable to follow an inner shape of the body cavity and the like, by a user performing a bending operation at an operation section.

Also, a light guide for guiding illumination light is inserted through from the operation section of the endoscope to a tip end portion of the insertion portion. Moreover, in some cases, an image guide for guiding reflected light from a subject is also inserted therethrough. Further, the operation section is provided with an eyepiece portion allowing for observing with the naked eyes the light of the subject guided through the image guide, and a connection portion of a light source device, for introducing predetermined illumination light into the light guide.

Different types of endoscopes include an electronic endoscope wherein a solid-state image-pickup device is placed at the tip end portion of the insertion portion, or at a tip end of the image guide of the insertion portion, the solid-state image-pickup device capturing light of the subject, which is the illumination light projected from the light guide and reflected on the subject, so as to generate an image signal based on which an image of the subject is displayed on a monitor.

For an endoscope device using, for example, a microprocessor, which is configured to include such an endoscope, various techniques have conventionally been proposed relating to an endoscope device having a circuit for maintaining controlled apparatuses in a safe status against malfunction of the microprocessor, in, for example, Japanese Patent Application Laid-Open No. 4-40014, and the like.

SUMMARY OF THE INVENTION

The endoscope control device of the present invention includes: a safety maintaining circuit for maintaining safety in terms of function or use-purpose of the endoscope control device; a control section for controlling operation of the endoscope control device; and an activation section for activating the control section, wherein the safety maintaining circuit is formed in the same device as at least one of the control section and the activation section.

Advantages of the present invention will become further apparent from the following detailed description.

DETAILED DESCRIPTION OF PREFERRED EMBODIMENTS

The following embodiments will be described in an example of a circuit relevant to operation of a lamp unit of a light source device of an endoscope device as a medical apparatus.

First Embodiment

Figure 1:
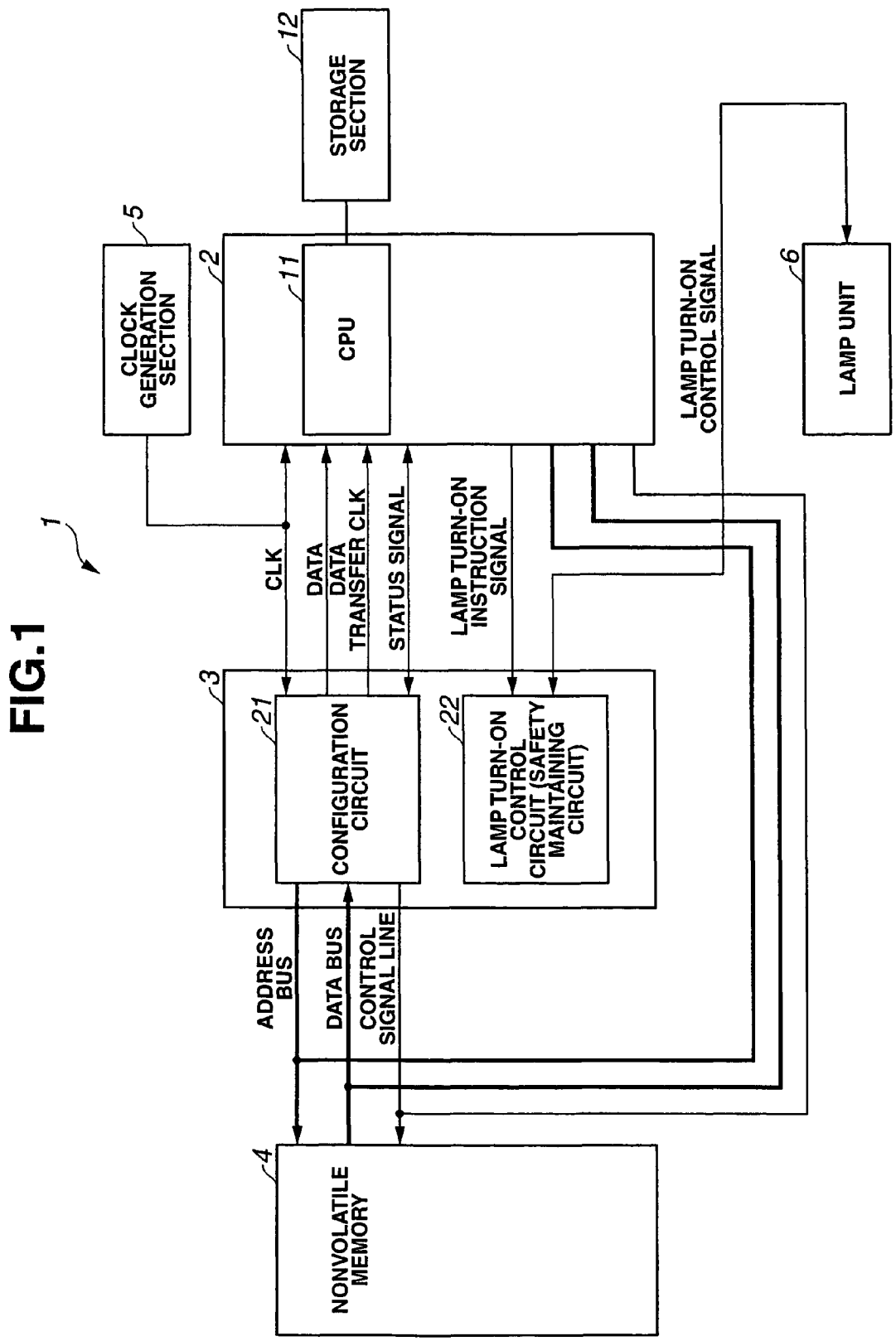
FIG. 1 is a block diagram showing a part of a configuration of a light source device of an endoscope device according to a first embodiment of the present invention.

FIG. 1 is a block diagram showing a part of a configuration of a light source device 1 of an endoscope device. The light source device 1 configures one part of an endoscope control device which is a medical apparatus. Although the light source device 1 typically includes various components such as a lamp, a filter, and a diaphragm, the present embodiment, a circuit relevant to turn-on control of the lamp will be mainly described for ease of explanation.

The light source device 1 is configured to include a control section 2, an activation section 3, a nonvolatile memory 4, and a clock generation section 5. The control section 2, which is control means for controlling operation of the light source device 1, is realized by an FPGA (Field Programmable Gate Array) which is a one-chip semiconductor device. As will be described later, the control section 2 (FPGA) includes inside thereof a central processing unit (hereinafter referred to as CPU) 11, a serial-parallel circuit, and peripheral circuits of the CPU 11 that perform buzzer control and the like. Written to the control section 2 is configuration data read out from the nonvolatile memory 4 which is nonvolatile storage means and a nonvolatile storage section. The control section 2 has what is called a SRAM structure, and data stored therein is erased when the power is turned off. A storage section 12 is a memory area required for the CPU 11 to operate.

The control section 2 writes the configuration data in the activation section 3 to construct therein various function execution sections.

The light source device 1 has an automatic turn-on mode in which the lamp is automatically lighted on after the light source device 1 is activated, and a manual turn-on mode in which the lamp is lighted on with a press of a lamp button after the light source device 1 is activated. Regardless of the automatic turn-on mode or the manual turn-on mode, when the lamp lights on, a status signal such as of breaking, adherence and the like of the lamp is input from the lamp unit 6 to the CPU 11 in the control section 2. Because the status signal takes some time to stabilize, in the present embodiment, the light source device 1 is configured to flash an LED on a front panel from when the lamp button is pressed until the status signal stabilizes.

Moreover, the light source device 1 is connected to an external apparatus, and also operates interlocked with the external apparatus. If the external apparatus and the light source device 1 both generates an operation sound when the user operates the external apparatus or the light source device 1, it is concerned that the user may be perplexed. Therefore, in the present embodiment, if an operation is made when the light source device 1 is connected to the external apparatus, either the external apparatus or the light source device 1 generates an operation sound.

Figure 2:
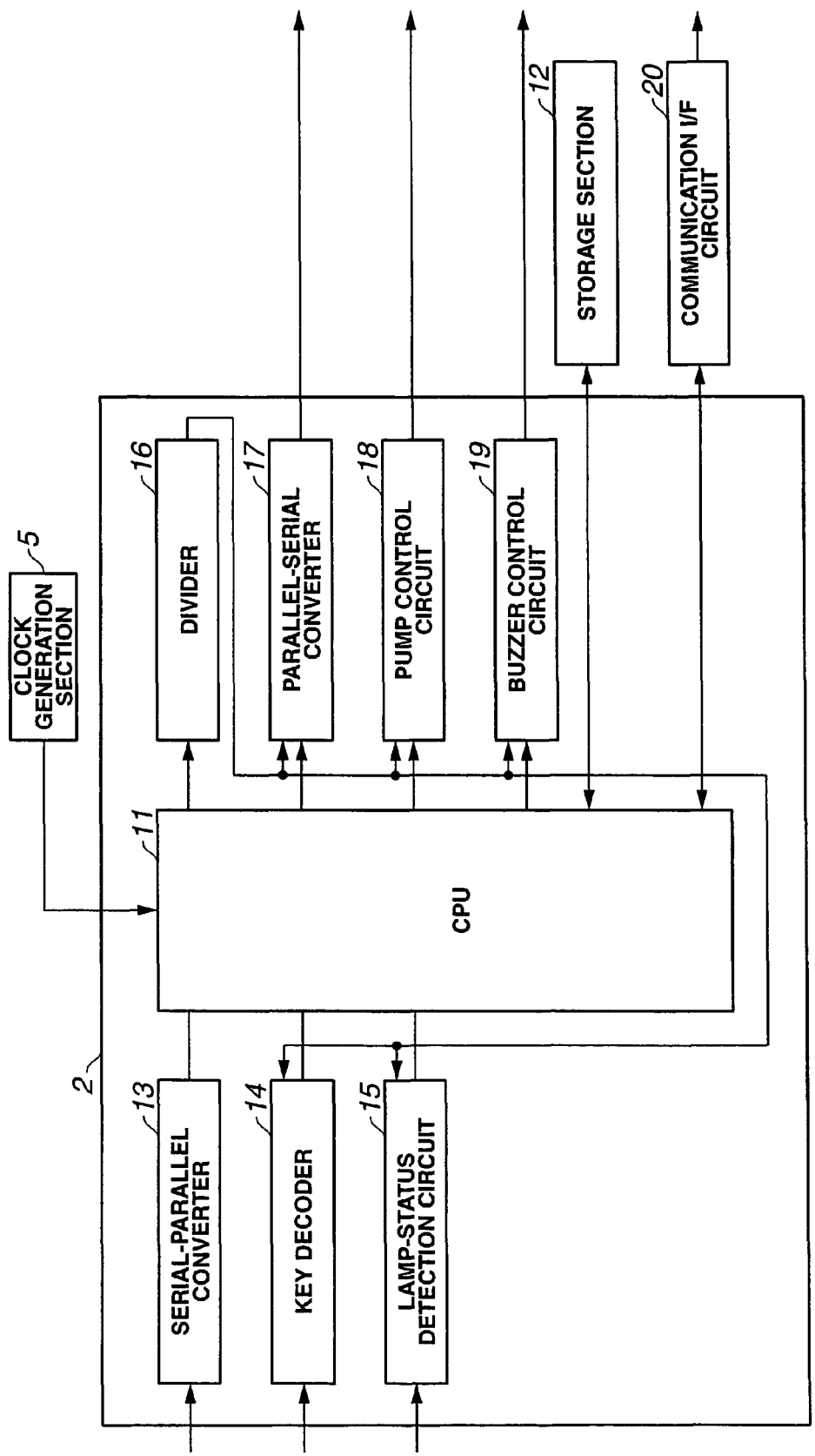
FIG. 2 is a block diagram showing a configuration of a control section in which various function execution sections are constructed according to a first embodiment of the present invention.

FIG. 2 is a block diagram showing a configuration of the control section 2 in which various function execution sections are constructed. The control section 2, which is an FPGA, includes circuits constructed by the configuration data written therein, i.e., the CPU 11 and various peripheral circuits connected to the CPU 11. In the present embodiment, shown as the peripheral circuits are a serial-parallel converter 13, a key decoder 14, a lamp-status detection circuit 15, a divider 16, a parallel-serial converter 17, a pump control circuit 18, and a buzzer control circuit 19. Further, the CPU 11 is connected to a communication interface (I/F) circuit 20 for communicating with an external apparatus.

As described above, the control section 2 is a one-chip semiconductor device called FPGA, whose internal configuration is determined based on the configuration data stored in the nonvolatile memory 4. When an electric power is supplied to and the configuration data is written to the control section 2, the various circuits such as the serial-parallel converter 13 are constructed in the control section 2. The configuration data is internal circuit configuration data to determine an internal circuit configuration of the control section 2. The configuration data in the present embodiment is specifically circuit configuration data for configuring the CPU 11 and various peripheral circuits thereof in the control section 2.

In FIG. 2, a clock signal CLK from the clock generation section 5 is supplied to the CPU 11, and then is further divided by the divider 16 into a pulse having a predetermined cycle. The divided clock is supplied to the peripheral circuits, i.e., the decoder 14, the lamp-status detection circuit 15, the parallel-serial converter 17, the pump control circuit 18, and the buzzer control circuit 19.

Also, the activation section 3, which is activation means for activating the control section 2, is realized by a CPLD (Complex Programmable Logic Device) which is a one-chip semiconductor device. The activation section 3 integrally includes a configuration circuit 21 and a lamp turn-on control circuit 22.

The configuration circuit 21 reads predetermined configuration data from the nonvolatile memory 4, and writes the configuration data into the control section 2 as serial data. Specifically, the configuration circuit 21 is connected to the nonvolatile memory 4 via an address bus, a data bus, and a control signal line. Also, the configuration circuit 21 is connected to the control section 2 via a data line, a data transfer clock (CLK) signal line, and a status signal line. Thus, the configuration circuit 21 can read the configuration data from the nonvolatile memory 4 and write the data into the control section 2.

The lamp turn-on control circuit 22 receives a lamp turn-on instruction signal from the control section 2 via a predetermined signal line, and outputs a lamp turn-on control signal to the lamp unit 6 including a lamp, according to the lamp turn-on instruction signal received. The lamp turn-on control circuit 22 includes a safety maintaining circuit for realizing a function of observation by the endoscope, or a function of keeping the lamp turned on for maintaining or ensuring safety in terms of use-purpose of the endoscope, even if the CPU 11 of the control section 2 is crashed or a reset signal is erroneously input to the CPU 11. In other words, the safety maintaining circuit as safety maintaining means performs a safety maintaining function for maintaining safety, of performing a predetermined checking operation to be described later, on receiving a lamp turn-off instruction signal from the control section 2 when the device is normally operating, to check that the lamp turn-off instruction signal is normally generated, and then outputting a lamp turn-off control signal to the lamp unit 6.

Because the activation section 3 is realized by a CPLD, the lamp turn-on control circuit 22 having the safety maintaining circuit is also realized by a connection of a logic circuit on the one-chip semiconductor device.

The FPGA and the CPLD are each a device including a programmable logic circuit. More precisely, the FPGA is a field programmable gate array, and the CPLD is a programmable logic IC chip having a gate with a larger scale than a PLD. The PLD is a digital IC chip in which an AND gate, an OR gate, and the like, are provided inside in advance and internal connections thereof are electrically modified to realize a desired logic.

The foregoing has described a part of the functions of the light source device 1. The light source device 1 functioning as a part of the endoscope device performs not only operations of turning on and off the lamp, but also control of a filter, a diaphragm, or the like, according to various operations by a surgeon operating the endoscope.

For example, in the light source device 1, a particular light filter transmitting only a light in a specific frequency range can be placed on the optical axis of the illumination light. Placing this particular light filter on the optical axis of the illumination light can render visible portions invisible with a normal light.

In the light source device 1, a light decreasing mesh for decreasing the total radiation light amount depending on a connected endoscope, can also place on the optical axis. In the case that the particular light filter caused an insufficient total radiation light amount, the light decreasing mesh is controlled to modify transmissivity thereof, to allow for preventing thermal burn of the endoscope during illumination operation.

Thus, the light source device 1 performs various controls depending on the various functions, and during the various controls, the control section 2 reads various necessary data and the like from the nonvolatile memory 4, and uses the data to execute a predetermined control program.

Now, an operation of the light source device 1 according to the above-described configuration will be described. First, an operation under a normal status is described.

When the light source device 1 is powered on, first the configuration circuit 21 of the activation section 3 reads the configuration data from the nonvolatile memory 4. Then, the configuration circuit 21 sends the read configuration data to the control section 2 in a serial signal via the data line, based on a data transfer clock CLK signal. Because of being an FPGA, the control section 2 constructs therein the CPU 11 and the various peripheral circuits as shown in FIG. 2, based on the written configuration data.

After the CPU 11 is constructed in the control section 2, the CPU 11 performs an initialization processing, and the control section 2 performs various predetermined functions.

The CPU 11 monitors the switch status of the front panel not shown of the light source device 1. When detecting via the key decoder 14 that a lamp switch of the front panel is turned on, the CPU 11 outputs a lamp turn-on instruction signal to the lamp turn-on control circuit 22 in the activation section 3. On receiving the lamp turn-on instruction signal, the lamp turn-on control circuit 22 outputs the lamp turn-on control signal to the lamp unit 6.

As mentioned above, the lamp turn-on control circuit 22 includes the safety maintaining circuit for continuously keeping the lamp turned on, when, for example, the CPU 11 is crashed, a reset signal is erroneously input to the CPU 11, or a noise signal is input to the CPU 11, with the lamp turned on. As mentioned above, the safety maintaining circuit is constructed in the activation section 3 as a part of the functions of the CPLD. Thus, the lamp turn-on control circuit 22 is configured to prevent the lamp from being turned off, even if the CPU 11 is, for example, crashed, when, for example, a medical treatment is being performed using an endoscope.

When, for example, receiving the lamp turn-off instruction signal, the safety maintaining circuit performs a predetermined communication with the CPU 11 and determines whether or not the CPU 11 is normally operating, depending on whether the communication is normally operated and normally ended. If the predetermined communication with the CPU 11 does not normally end, the safety maintaining circuit determines the CPU 11 is not normally operating, and does not output a lamp control signal for turning off the lamp to the lamp unit 6. Then, the safety maintaining circuit maintains an output signal of the lamp turn-on control circuit 22 in the turned-on status. As a result, the lamp will not be turned off even if the CPU 11 is, for example, crashed when the surgeon is performing a medical observation or treatment, and therefore the surgeon can continue the observation and the like.

The predetermined communication is a communication in which, for example, a sending request for predetermined data is outputted from the safety maintaining circuit to the CPU 11 a plurality of times, and the safety maintaining circuit receives the predetermined data, all the plurality of times. If incapable of receiving the predetermined data all the plurality of times, the safety maintaining circuit prohibits outputting a lamp turn-off control signal for turning off the lamp.

It is to be noted that a method of checking processing for maintaining safety in the safety maintaining circuit is not limited to the aforementioned communication method, but may employ other methods or configurations.

Next, an operation when the safety maintaining circuit has a failure will be described.

As described above, when the light source device 1 is powered on, first the configuration circuit 21 of the activation section 3 reads the configuration data from the nonvolatile memory 4. However, if the semiconductor device of the CPLD configuring the activation section 3 is, for example, broken for some reason, then the safety maintaining circuit is also broken and has a failure, and at the same time, the configuration circuit 21 configured by the CPLD is also broken and inoperative. As a result, the CPU 11 of the control section 2 will not be constructed when the light source device 1 is powered on, and therefore the light source device 1 will not be activated. Accordingly, it is prevented that the surgeon, a user, uses a broken safety maintaining circuit.

That is, because the one-chip semiconductor device called the CPLD of the activation section 3 includes the safety maintaining circuit, if the safety maintaining circuit is, for example, broken and has a failure, then the configuration circuit 21 of the same activation section 3 also has a failure and is inoperative, and therefore the control section 2 is not constructed. In other words, because the safety maintaining circuit is formed in the same device as the activation section 3, if the device is broken, then control section 2 is not constructed. Thus, the user, e.g., the surgeon, can recognize that the light source device 1 is abnormal, when powering on the device, i.e., before performing a medical treatment and the like.

It is to be noted that the activation section 3, although configured by the CPLD in the above-mentioned example, may be configure by the FPGA.

Moreover, even when the above-mentioned activation section 3 is normally activated and the CPU 11 and the like of the control section 2 is normally constructed, an activation permission signal may be supplied from the lamp turn-on control circuit 22 to the CPU 11 of the control section 2, before starting performing the various functions of the control section 2. When supplied with electric power and normally activated, the lamp turn-on control circuit 22 supplies the activation permission signal to the CPU 11 after the passage of a predetermined time period after the activation. The activation permission signal is supplied to, for example, an input terminal for a reset signal of the CPU 11.

As a result, if after the control section 2 including the CPU 11 is normally constructed by the configuration circuit 21, the lamp turn-on control circuit 22 including the safety maintaining circuit normally operates, and the activation permission signal is not supplied to the CPU 11 as a predetermined signal, then a CPU activation permission signal is not inputted to the CPU 11 and resetting of the CPU 11 is not cancelled, which results in the light source device 1 not activated. On the contrary, if the activation permission signal is supplied to the CPU 11, the CPU activation permission signal is inputted to the CPU 11 and the resetting of the CPU 11 is cancelled, which results in the light source device 1 activated.

Such a configuration allows for double checking of the safety maintaining circuit.

Second Embodiment

Figure 3:
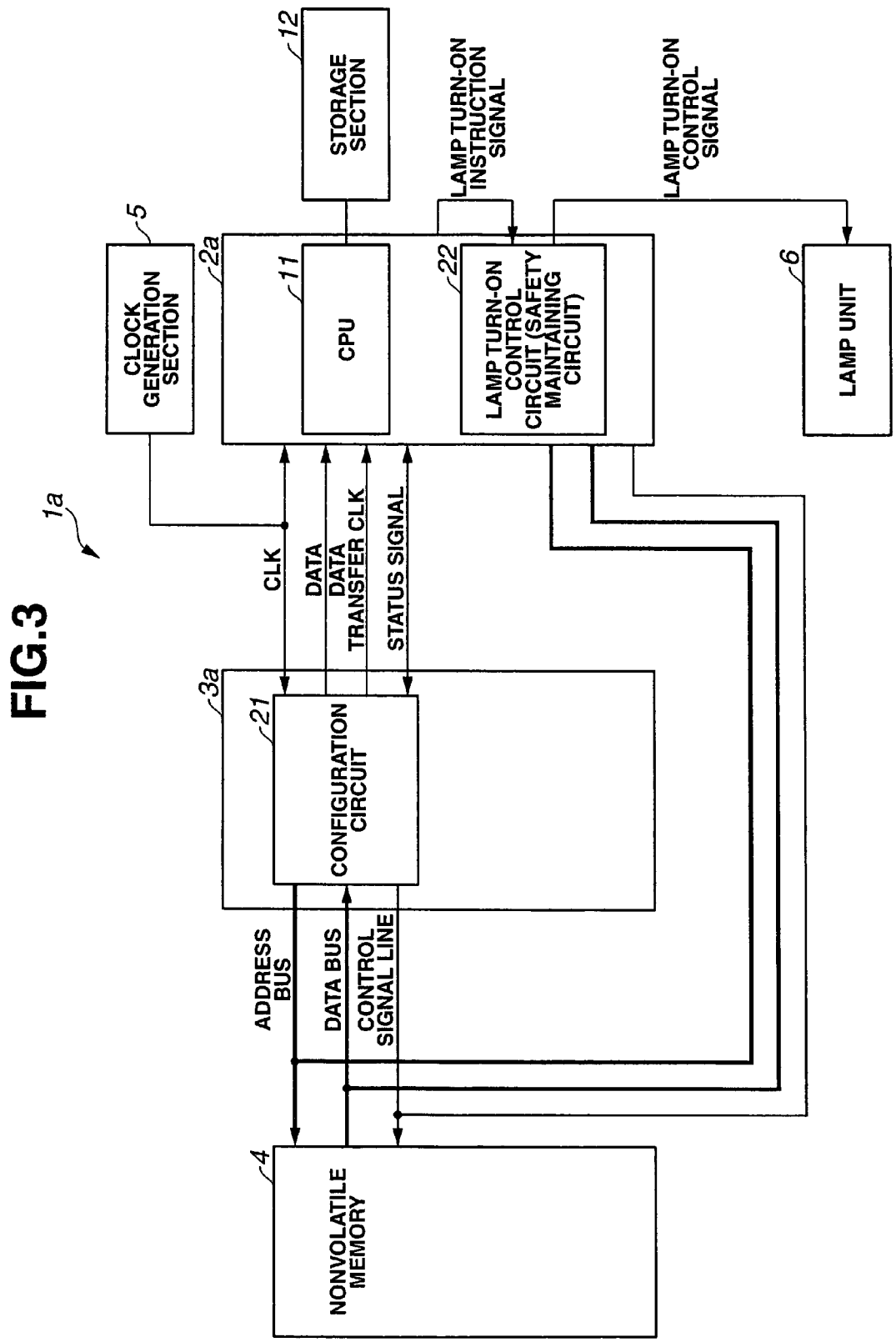
FIG. 3 is a block diagram showing a part of a configuration of a light source device of an endoscope device according to a second embodiment of the present invention.
Figure 4:
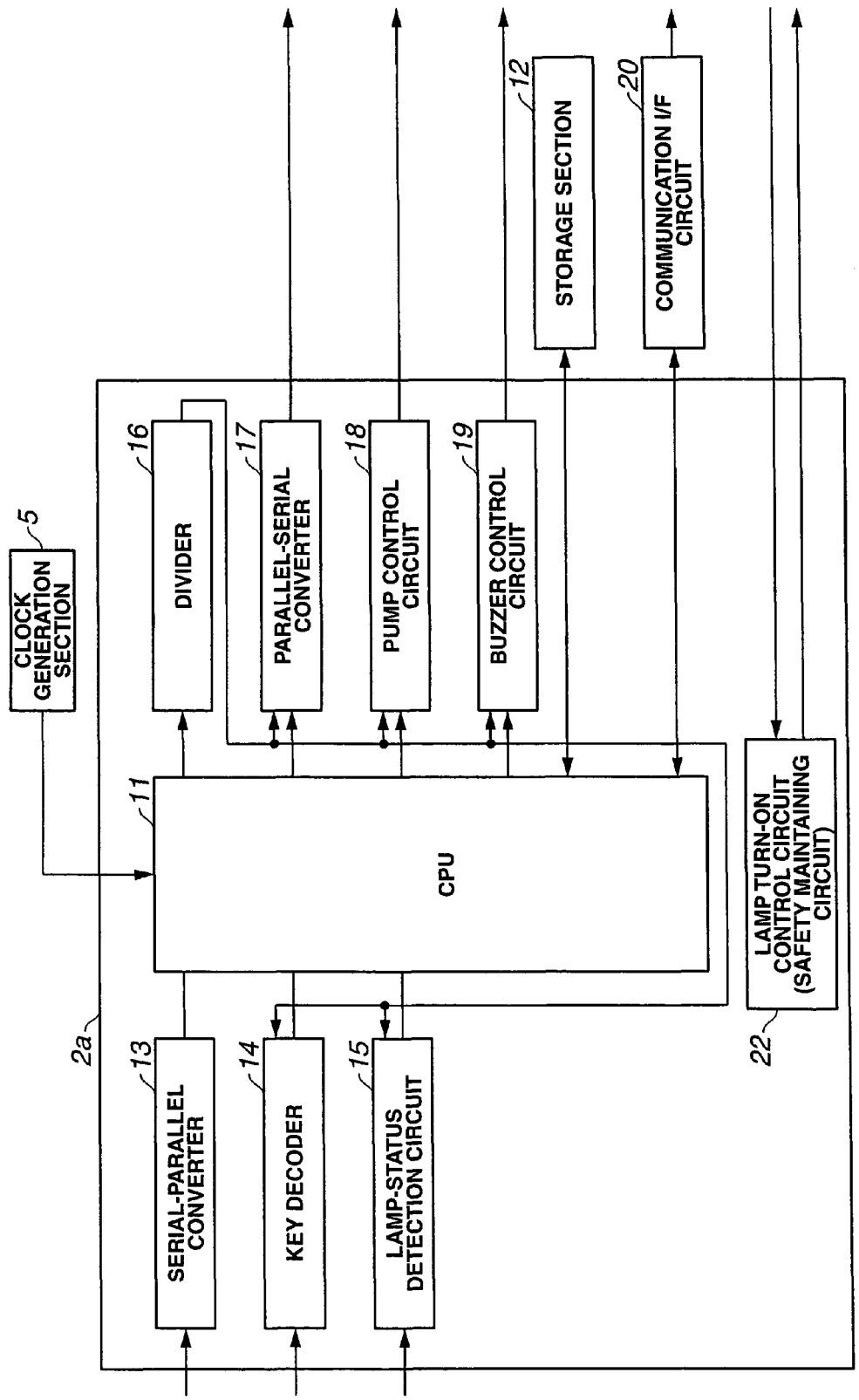
FIG. 4 is a block diagram showing a configuration of a control section in which various function execution sections are constructed according to a second embodiment of the present invention.

FIGS. 3 and 4 are a block diagrams each showing a part of a configuration of a light source device 1a according to a second embodiment of the present invention. FIG. 4 is a block diagram showing a configuration of a control section 2a in which various function execution sections are constructed. The same components as in the first embodiment are attached with the same symbols and descriptions thereof will be omitted.

This embodiment differs from the first embodiment in configuration in that the lamp turn-on control circuit 22 is included not in an activation section 3a but in a control section 2a of the FPGA integrally with the CPU 11. Therefore, the lamp unit 6 is controlled to be lit on and off by the lamp turn-on control signal from the lamp turn-on control circuit 22 in the control section 2a.

An operation of the light source device 1a according to the above-mentioned configuration will be described.

When the light source device 1a is powered on, first the configuration circuit 21 in the activation section 3a reads the configuration data from the nonvolatile memory 4. Then, the configuration circuit 21 sends the read configuration data to the control section 2a. The control section 2a, because of being an FPGA, constructs therein the CPU 11 and various peripheral circuits as shown in FIG. 4, based on the written configuration data if the data is normal. After the CPU 11 is constructed in the control section 2a, the CPU 11 performs initialization processing and the control section 2a performs various predetermined functions.

The CPU 11 outputs a lamp turn-on instruction signal to the lamp turn-on control circuit 22 in the control section 2a. On receiving the lamp turn-on instruction signal, the lamp turn-on control circuit 22 outputs the lamp turn-on control signal to the lamp unit 6. The lamp turn-on control circuit 22 is configured to include the safety maintaining circuit. As mentioned above, the safety maintaining circuit is constructed in the control section 2a as a part of the functions of the FPGA.

As described above, when the light source device 1 is powered on, first the configuration circuit 21 of the activation section 3 reads the configuration data from the nonvolatile memory 4. However, if the semiconductor device of the FPGA configuring the control section 2a is, for example, broken for some reason, then the safety maintaining circuit is also broken and has a failure, and at the same time, the CPU 11 configured by the FPGA is also broken and inoperative. As a result, even if the light source device 1 is powered on, the CPU 11 of the control section 2a is not constructed and thus the light source device 1 is not activated. Therefore, the surgeon or the user is prevented from using a broken safety maintaining circuit.

That is, because the safety maintaining circuit is included in the semiconductor device called the FPGA in the control section 2a, when the safety maintaining circuit is, for example, broken and has a failure, also the CPU 11 in the same control section 2a is not constructed and is inoperative. In other words, because the safety maintaining circuit is formed in the same device as the control section 2a, if the device is broken, then control section 2a is not operated. Therefore, the user such as the surgeon can recognize that the light source device 1 is abnormal, when powering on the device, i.e., before performing a medical treatment, and the like.

It is to be noted that the activation section 3, although configured by the CPLD in the above-mentioned example, may be configure by the FPGA.

Now, a method will be described for preventing the CPU of the light source device from being activated when the safety maintaining circuit is abnormal.

As described above, if the light source device is activated or operated once even when the safety maintaining circuit of the light source device is abnormal, then the safety maintaining circuit will not function afterward when it should, disallowing the user to continue observation and the like using the endoscope.

Figure 5:
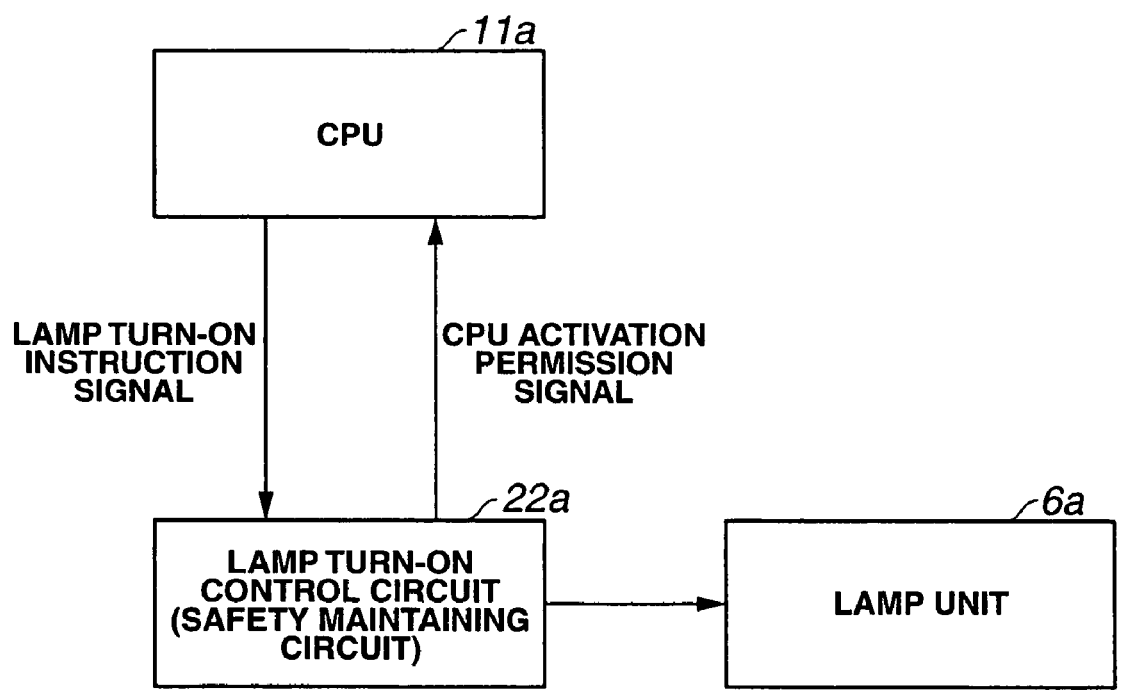
FIG. 5 is a block diagram to illustrate a configuration for preventing a CPU from being activated even if the CPU is not broken, when a safety maintaining circuit is abnormal.

Therefore, the CPU is prevented from being activated even if the CPU is not broken when the safety maintaining circuit is abnormal. FIG. 5 is a block diagram to illustrate a configuration for preventing the CPU from being activated even if the CPU is not broken when a safety maintaining circuit is abnormal.

As shown in FIG. 5, a lamp turn-on control circuit 22a having the safety maintaining circuit, on receiving the lamp turn-on instruction signal from a CPU 11a, supplies the lamp turn-on control signal to a lamp unit 6a in response to the lamp turn-on instruction signal.

Further, the light source device is configured such that the lamp turn-on control circuit 22 supplies the activation permission signal to the CPU 11a. In particular, the lamp turn-on control circuit 22a is configured to supply the activation permission signal to the CPU 11a, after the lamp turn-on control circuit 22a is normally activated. In the present embodiment, the activation permission signal is supplied to an input terminal for a reset signal of the CPU 11a.

That is, when supplied with electric power and normally activated, the lamp turn-on control circuit 22a supplies the activation permission signal as a reset cancelling signal to the CPU 11a, after the passage of a predetermined time period after the activation.

As a result, the lamp turn-on control circuit 22a is normally operated and the activation permission signal as a predetermined signal is not supplied to the CPU 11a. Then, resetting of the CPU 11a is not cancelled, and therefore the CPU 11a is not activated. On the contrary, if the activation permission signal is supplied to the CPU 11a, then the CPU activation permission signal is inputted thereto and the resetting of the CPU 11a is cancelled, which activates the CPU 11a.

With such a configuration, the CPU 11a is not activated if the safety maintaining circuit is abnormal, and therefore the user can recognize that the light source device 1 is abnormal when powering on the device, i.e., before operating a medical treatment and the like.

It is to be noted that, although the foregoing has described, for ease of description, an example of the safety maintaining circuit of the lamp turn-on control circuit of the light source device, the configuration of each of the above-described embodiments of the present invention may be applied to other circuits of the light source device, e.g., a safety maintaining circuit of an air and water feeding pump control circuit, and the like.

When applied with the configurations of the present invention, the air and water feeding pump control circuit operates to keep operating a pump for feeding air into the body, even if the light source device of the endoscope device is abnormal. As a result, the lamp and the air will continue lighting and feeding, respectively, which allows the user and the like to continue observation and the like using the endoscope.

As described above, according to each of the present embodiments, the light source device is not activated when the safety maintaining circuit is abnormal. Therefore, it is prevented that the safety maintaining circuit becomes inoperative when the surgeon is performing a medical observation, treatment, and so on.

It should be noted that the present invention may be applied not only to an endoscope control device in the medical field, but also to one in the industrial field.

The present invention is not limited to the above-described embodiments, but may be subject to various modifications, changes and so on, within the gist of the present invention.

It is obvious that, in the present invention, embodiments differing in a wide scope may be configured based on the present invention, without departing from the spirit and scope of the present invention. The present invention is not restricted by any specific embodiment thereof except being limited by the appended claims.

What is claimed is:

1. An endoscope control device, comprising:
   a safety maintaining circuit for maintaining safety in terms of function or use-purpose of the endoscope control device;
   a control section for controlling operation of the endoscope control device, the control section being a one-chip first semiconductor device and constructed based on circuit configuration data; and
   an activation section for activating the control section by writing the circuit configuration data into the control section, the activation section being a one-chip second semiconductor device which is different from the first semiconductor device,
   wherein the safety maintaining circuit is included in the first semiconductor device or the second semiconductor device, and when the safety maintaining circuit has a failure, the control section is not constructed.

2. The endoscope control device according to claim 1, wherein the first semiconductor device and the second semiconductor device are a semiconductor device comprising a programmable logic circuit.

3. The endoscope control device according to claim 2, wherein the first semiconductor device and the second semiconductor device are an FPGA or a CPLD.

4. The endoscope control device according to claim 1, further comprising a nonvolatile storage section storing circuit configuration data of the control section, wherein the activation section reads the circuit configuration data from the nonvolatile storage section, and writes the circuit configuration data into the control section.

5. The endoscope control device according to claim 1, wherein, when an abnormality occurs in the endoscope control device, the safety maintaining circuit maintains an output signal of a circuit in the endoscope control device.

6. The endoscope control device according to claim 5, wherein the safety maintaining circuit is a lamp turn-on control circuit.

* * * * *